(12) United States Patent
Biedermann et al.

(10) Patent No.: US 11,109,893 B2
(45) Date of Patent: Sep. 7, 2021

(54) BONE ANCHOR

(71) Applicant: BIEDERMANN TECHNOLOGIES GMBH & CO. KG, Donaueschingen (DE)

(72) Inventors: Timo Biedermann, Trossingen (DE); Berthold Dannecker, St. Georgen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 16/005,130

(22) Filed: Jun. 11, 2018

(65) Prior Publication Data

US 2018/0353213 A1    Dec. 13, 2018

Related U.S. Application Data

(60) Provisional application No. 62/552,154, filed on Aug. 30, 2017.

(30) Foreign Application Priority Data

Jun. 12, 2017   (EP) .................................... 17175538

(51) Int. Cl.
*A61B 17/70*   (2006.01)
*A61B 90/00*   (2016.01)

(52) U.S. Cl.
CPC ...... *A61B 17/7001* (2013.01); *A61B 17/7032* (2013.01); *A61B 17/7034* (2013.01);
(Continued)

(58) Field of Classification Search
CPC .. A61B 17/7083–7091; A61B 17/7001; A61B 17/7034; A61B 17/7035
See application file for complete search history.

(56) References Cited

U.S. PATENT DOCUMENTS 8,932,210 B2 *   1/2015   Woods ............... A61B 17/7085
                                                                600/201
9,198,698 B1 *   12/2015   Doose .................. A61B 17/708
(Continued)

FOREIGN PATENT DOCUMENTS

EP    3 106 110 A1    10/2017
EP    3 106 110 B1    10/2017
(Continued)

OTHER PUBLICATIONS

Extended European Search Report for Application No. 17175538.2, dated Dec. 4, 2017, 11 pages.

*Primary Examiner* — Nicholas J Plionis
(74) *Attorney, Agent, or Firm* — Lewis Roca Rothgerber Christie LLP

(57) ABSTRACT

A bone anchor includes a shank for anchoring to a bone and a receiving part for coupling a rod to the shank. The receiving part includes a base and two legs each including a first portion extending away from the base, and a second portion extending from the first portion further away from the base, and an elongate extension member extending from the second portion still further away from the base. An internal engagement structure is provided on the first and second portions for engaging a fixation device. A breakaway portion facilitates breaking away of the second portion. The extension members are at least as long as the second portions. The second portions are stiffer than a region of the extension members adjacent the second portions.

24 Claims, 4 Drawing Sheets

(52) U.S. Cl.
CPC ...... *A61B 17/7035* (2013.01); *A61B 17/7085* (2013.01); *A61B 2090/037* (2016.02)

(56) References Cited

U.S. PATENT DOCUMENTS

| | | | |
|---|---|---|---|
| 2006/0247658 A1 | 11/2006 | Pond, Jr. et al. | |
| 2009/0221877 A1* | 9/2009 | Woods | A61B 17/7085 600/201 |
| 2009/0222044 A1* | 9/2009 | Gorek | A61B 17/7085 606/279 |
| 2011/0098755 A1* | 4/2011 | Jackson | A61B 17/8685 606/305 |
| 2013/0103096 A1* | 4/2013 | Miller | A61B 17/7032 606/305 |
| 2014/0330315 A1* | 11/2014 | Butler | A61B 17/7002 606/278 |
| 2015/0094781 A1* | 4/2015 | Paroth | A61B 17/8605 606/86 R |
| 2015/0164569 A1* | 6/2015 | Reitblat | A61B 17/7079 606/279 |
| 2015/0173809 A1* | 6/2015 | Bechtel | A61B 17/7002 606/265 |
| 2016/0008034 A1* | 1/2016 | Stokes | A61B 17/7085 606/278 |
| 2016/0367295 A1* | 12/2016 | Biedermann | A61B 17/7032 |

FOREIGN PATENT DOCUMENTS

| | | |
|---|---|---|
| EP | 2 881 053 A1 | 1/2018 |
| EP | 2 881 053 B1 | 1/2018 |

* cited by examiner

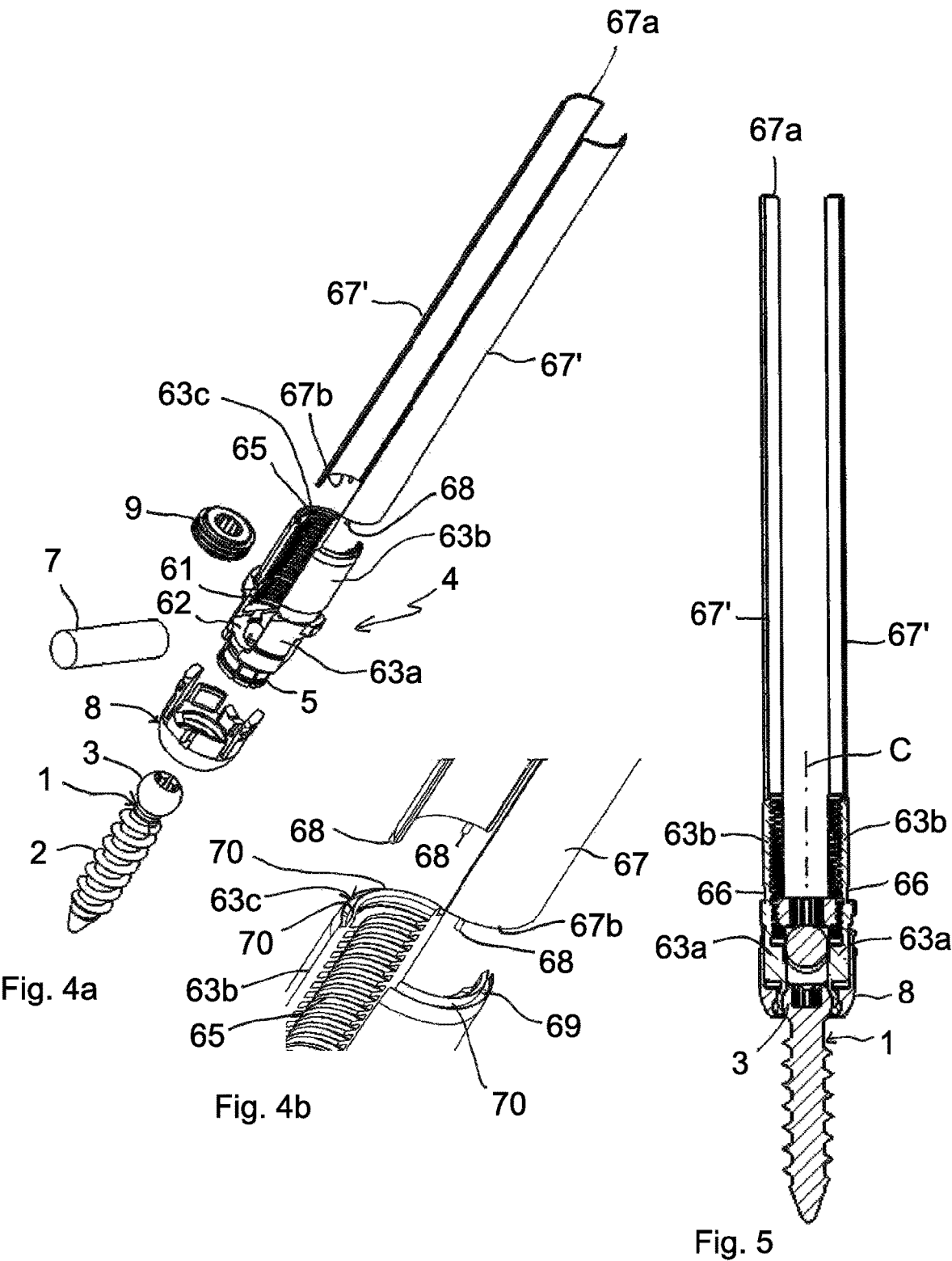

BONE ANCHOR

CROSS-REFERENCE TO RELATED APPLICATION(S)

The present application claims priority to and the benefit of U.S. Provisional Patent Application No. 62/552,154, filed Aug. 30, 2017, the contents of which are hereby incorporated by reference in their entirety, and claims priority from European Patent Application EP 17 175 538.2, filed Jun. 12, 2017, the contents of which are hereby incorporated by reference in their entirety.

BACKGROUND

Field

The invention relates to a bone anchor with extension members that is particularly suitable for minimally invasive surgery (MIS).

Description of Related Art

Various bone anchors suitable for MIS are known in the prior art that have extension members. Such bone anchors include a shank to be anchored in a bone and a receiving part with two free legs to receive a spinal rod therebetween. The legs may be provided with extension members by means of which the legs are extended to permit guiding and/or supplying elements of an implant or instruments to the implantation site.

US 2006/0247658 A1 describes an apparatus for guiding a surgical implant to a bone anchor during surgery which includes bone anchor extenders releasably attachable to the bone anchor, wherein the bone anchor extenders clip onto a head portion of the bone anchor to assist in guiding the surgical implant to the bone anchor. When the extenders are releasably attached to the bone anchor, the extenders can be elastically deformed and/or bent to widen or open the pathway defined by the extenders in which the implant or implant components can travel.

SUMMARY

In MIS, there is a need to provide surgical instrumentation for advancing and guiding implant components and/or instruments from outside the body to the implantation site. There is also a need for facilitating improved handling, reliability, and visibility of the components used therefor, and for reduction of soft tissue trauma.

Therefore it is an object of the invention to provide an improved bone anchor with extension members that addresses at least one of the above-mentioned needs.

According to an aspect of the invention, a bone anchor includes at least a shank for anchoring in a bone or a vertebra and a receiving part for receiving a rod. The receiving part includes a recess by means of which two free legs are formed for inserting the rod therebetween, and a bore with a bore axis. The legs have a first portion extending from the base of the recess to a first distance above the base and a second portion extending from an end of the first portion towards a second distance from the base greater than the first distance. An internal thread is formed in at least a section of each of the first portion and the second portion. Between the first and the second portion a break-away portion is formed that permits breaking away of the second portion from the first portion. The legs each includes an extension member extending from an end of the second portion to a third distance from the base of the recess. A stiffness of the extension member is less than a stiffness of the first and/or the second portion of the legs.

As the stiffness of the extension members of the legs is smaller than the stiffness of the second and first portions of the legs, the extension members of the legs can be spread apart. This facilitates improving the view onto the implantation site during surgery. The second portions of the legs that are broken away after fixation of the bone anchor, however, have sufficient strength and stiffness for facilitating manipulations performed with instruments during surgery and safely guiding implant components.

An advantage of this design may also be that the extension members form one part together with the second portion of the legs and can be broken away together with the second portion of the legs after final fixation of the bone anchor. Due to the lower stiffness of the extension members a risk of accidental break-off between the first and the second portions of the legs is reduced, and also the soft tissue is less affected.

The reduced stiffness of the extension members may be obtained in several ways, such as by reducing a wall thickness of the extension members compared to a wall thickness of the second and first portions of the legs. Another option is to provide one or more recesses in the wall of the extension members that render the extension members more flexible. Preferably, an inner wall of the extension members is threadless. Thus, a thread is only provided in the second and the first portions of the legs that have sufficient stiffness to securely permit the insertion of, for example, a set screw for fixation of the rod and/or the entire bone anchor.

The extension members may be bonded (or fused) to the second portions of the legs. Alternatively, the extension members may be releasably mounted to the second portions of the legs. The connection between the extension members and the second portions of the legs may be a form-fit connection. Combinations of form-fit connection and bonding may also be contemplated. The extension members may be made of the same or of a different material compared to the first and second portions of the legs. For example, using a material that has a lower modulus of elasticity also may contribute to making the extension members more flexible compared to the second and first portions of the legs.

The bone anchor may be implemented as a monoaxial bone anchor where the shank and the receiving part are fixedly connected to each other, for example, formed monolithically. The bone anchor may also be implemented in a polyaxial bone anchor, where the receiving part that has the legs and the extension members is pivotably connected to the shank.

An outer diameter of the bone anchor in the region of the extension members is smaller than or the same as in the region of the second portions and/or the first portions of the legs. Thereby, the bone anchor has a low profile in a radial direction that is particularly advantageous for MIS. Also, engaging the bone anchor with an instrument from a bottom of the bone anchor is facilitated. This is particularly useful in the case of the bottom loading polyaxial bone anchor where an anchoring element is inserted into the receiving part from a bottom end thereof. Moreover, a bulky construction is avoided, whereby it is possible to use the bone anchor also in regions of the human spine where the available space is limited, such as in the cervical region of the spine.

In an embodiment, the stiffness of the extension members against bending in a direction perpendicular or substantially perpending to the bore axis is smaller than the stiffness of the second portion and/or the first portion of the legs. In a still further embodiment, the extension members are torsionally flexible.

BRIEF DESCRIPTION OF THE DRAWINGS

Further features and advantages of the invention will become apparent from the description of embodiments by means of the accompanying drawings. In the drawings:

FIG. 4a shows a perspective exploded view of a second embodiment of a bone anchor.

FIG. 4b shows an enlarged view of a detail of FIG. 4a.

FIG. 5 shows a cross-sectional view of the bone anchor of FIG. 4a, the cross-section taken in a plane including a bore axis of a receiving part of the bone anchor and extending through a center of legs of the bone anchor.

DETAILED DESCRIPTION

Figure 1:
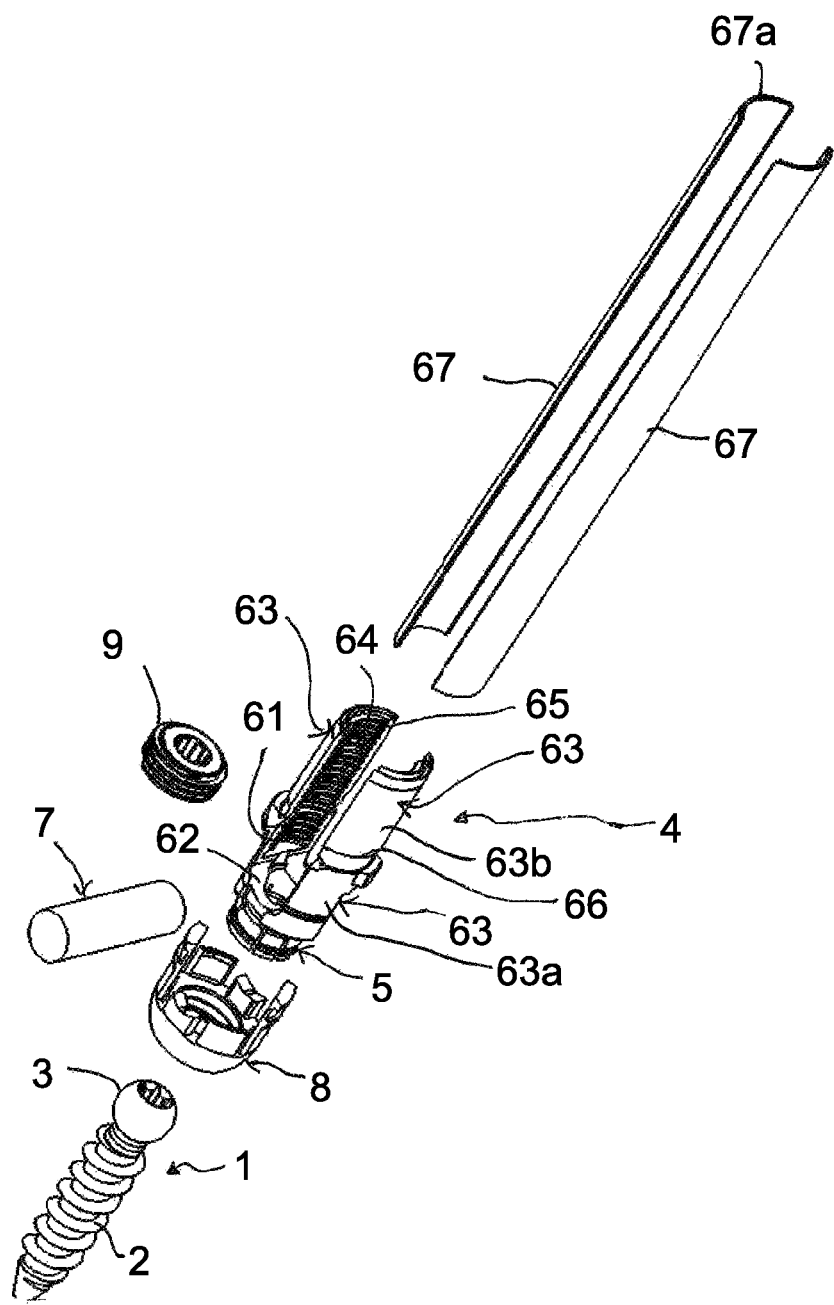
FIG. 1 shows a perspective exploded view of a first embodiment of a bone anchor.
Figures 2, 3:
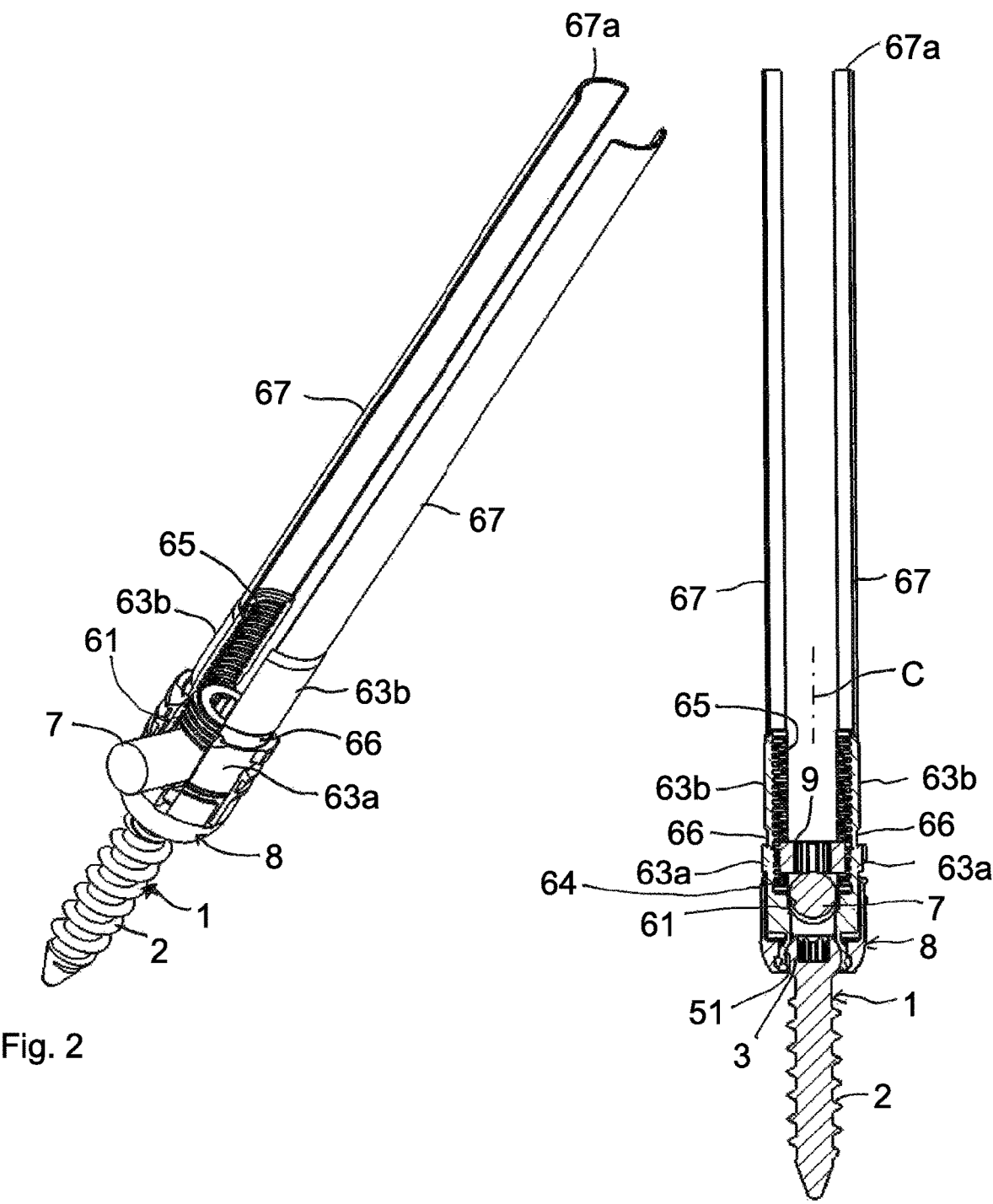
FIG. 2 shows a perspective view of the bone anchor of FIG. 1 in an assembled state.
FIG. 3 shows a cross-sectional view of the bone anchor of FIGS. 1 and 2, the cross-section taken in a plane including a bore axis of a receiving part of the bone anchor and extending through a center of legs of the bone anchor.

Referring to FIGS. 1 to 3, in a first embodiment, the bone anchor is designed as a polyaxial bone anchor. The bone anchor includes an anchoring element 1 having a shank 2 that may be at least partially threaded and a head 3. Further, the bone anchor includes a receiving part 4 including a head receiving portion 5 that is configured to accommodate the head 3 of the anchoring element 1 therein in a pivotable manner, and a rod receiving portion 6 that is configured to receive a rod 7. Additionally, the bone anchor may include a locking ring 8 that is configured to encompass the head receiving portion 5 and to compress the head receiving portion 5 to lock the head 3 therein. A fixation screw 9 may be provided to fix the rod 7 in the rod receiving portion 6.

The rod receiving portion 6 of the receiving part 4 is formed as a substantially cylindrical part including a substantially U-shaped recess 61 that extends from a free end of the rod receiving portion 6 towards the head receiving portion. The bottom of the recess 61 forms a base 62 from which two opposite upstanding legs 63 extend. Moreover, a coaxial bore 64 is provided that extends from a free end of the receiving part 4 towards the base 62 of the recess 61. The coaxial bore 64 defines a bore axis C that forms also a central axis of the receiving part 4. An internal thread 65 is provided at at least a portion of an inner wall of the legs 63 in the region of the coaxial bore 64. The bore 64 is configured to allow insertion of the fixation screw 9. At a distance from the base 62, a circumferentially extending break-away portion 66 is formed in the wall of the legs 63. The break-away portion 66 divides the legs into a first portion 63a below the break-away portion 65 and extending to the base 62, and a second portion 63b extending above the break-away portion 66. At the break-away portion 66, a wall thickness of the legs 63 may be reduced in such a manner that the second portion 63b of the legs may be broken away from the first portion 63a. Any other means for permitting breaking away of the second portion from the first portion may be contemplated, such as, for example, perforations, etc. The internal thread 65 is provided along at least a portion of the first portion 63a and at least a portion of the second portion 63b of the legs 63 so that the fixation screw can be screwed down along the pathway defined by the second portion 63b and the first portion 63a of the legs 63.

From an end of the second portion 63b of the legs 63 that is opposite to the first portion 63a, extension members that can also be called extended tabs or extension tabs 67 are formed that are connected to the second portion 63b of the legs, respectively. As a result, as shown in FIGS. 2 and 3, the bone anchor has extended legs, with a total length such that the extension tabs 67 project to a point outside of the patient when the bone anchor is implanted. The extension tabs 67 are used to define a pathway to guide an implant component, for example, the rod 7 or the fixation screw 9, to the bone anchor at the implant site beneath the skin of the patient.

In the embodiment, the extension tabs 67 are shaped as hollow cylinder segments or tube segments, and are arranged coaxially around the bore axis C in prolongation of the first portion 63a and the second portions 63b of the legs 63. A length of the extended tabs 67 in an axial direction is at least such that when the bone anchor is inserted into the bone or a vertebra, a free end 67a of the extended tabs is located outside the patient's body. Preferably, the length of the extended tabs is at least the sum of the lengths of the first portion 63a and the second portion 63b of the legs.

The extended tabs 67 have a stiffness against bending that is smaller than a stiffness of the first portion 63a and second portion 63b of the legs 63. More specifically, the extended tabs 67 may be spreadable apart from each other by manual action or with the aid of an instrument during surgery, i.e., during normal operating conditions. In contrast thereto, the first portion 63a and the second portion 63b of the legs 63 may resist against spreading under normal operating conditions. In other words, the extended tabs 67 are flexible while the first and second portions of the legs are stiff and do not substantially flex under normal operating conditions. More preferably, the extended tabs 67 are elastically flexible, such that once they have been spread apart, they return back to the upright position as shown in FIGS. 2 and 3.

To achieve the flexibility, the extended tabs 67 can have a reduced wall thickness in a radial direction relative to the bore axis C, compared to a wall thickness of the first portion 63a and second portion 63b of the legs 63.

In the embodiment of FIGS. 1 to 3, the extended tabs 67 are bonded to a free end of the second portions 63b of the legs. Hence, the extended tabs 67 are fixedly connected to the second portions 63b.

An outer width in a plane perpendicular to the bore axis C of the bone anchor in the region of the extended tabs 67 is the same or preferably smaller than an outer width of the receiving part 4 in the region of the first portion 63a and the second portion 63b of the legs 63. This results in a low profile or small size of the bone anchor in a radial direction.

As depicted in particular in FIGS. 1 and 3, the head receiving portion 5 is slotted and provides an accommodation space 51 to accommodate the head 3, which can be inserted into the accommodation space 51 through an opening from a bottom side of the receiving part 4. The locking ring 8 may optionally serve to compress the head receiving portion 5 to clamp and finally lock the head 3 in the accommodation space 51.

Referring to FIGS. 4a, 4b, and 5, in a second embodiment, the extended tabs 67' are formed as separate parts that are connectable, preferably releasably connectable, to the legs 63 of the receiving part. To achieve this, a form-fit connection may be provided between a lower end 67b of the extended tabs 67' and an upper end 63c of the legs 63. The form-fit connection may include projections such as pins 68 that are configured to engage recesses 69, such as holes, in the upper end of the second portion 63b of the legs 63. The projections 68 and recesses 69 each may be provided either on the second portion 63b of the legs or on the extended tabs 67', or vice-versa, or combinations of projections and recesses may be formed on one side of the connection and the complementary structure on the other side of the connection. Additionally, a circumferential groove 70 may be provided at the free end of the second portion 63b of the legs in which the extended tabs engage. Thereby, the stability of the connection is improved. The extended tabs may be exchangeably provided, i.e., various types of extended tabs, for example having various flexibilities, may be connected to the bone anchor. Once connected, a permanent connection may also be achieved in this embodiment by bonding the extended tabs 67' to the second portion 63b of the legs 63.

Figure 6:
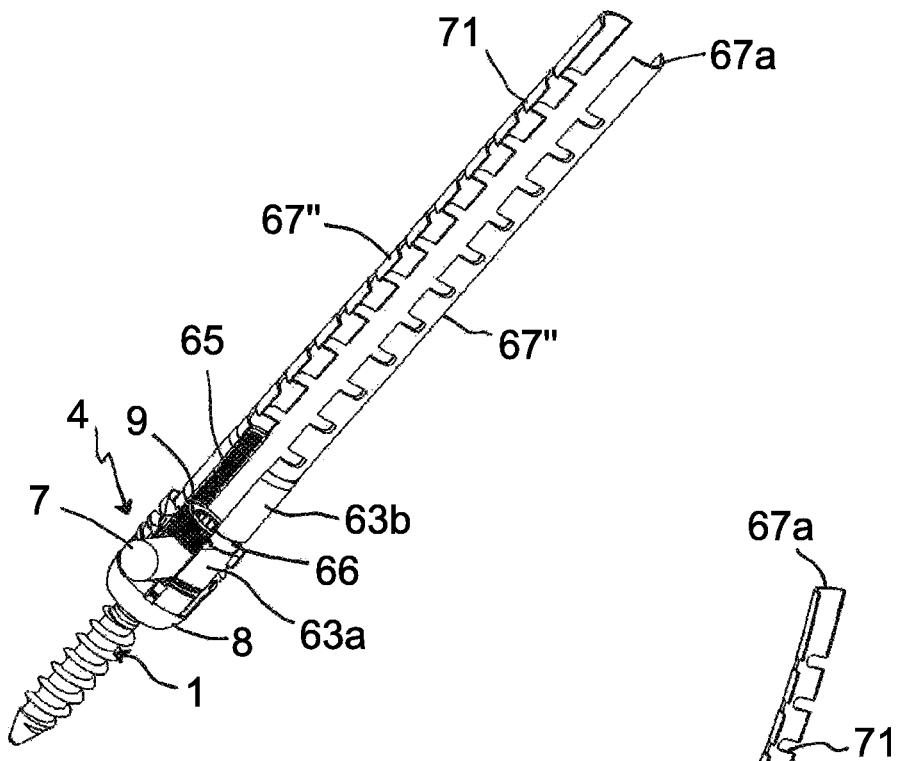
FIG. 6 shows a perspective view of a bone anchor according to a third embodiment in an assembled state and with extension members in a normal upright position.
Figure 7:
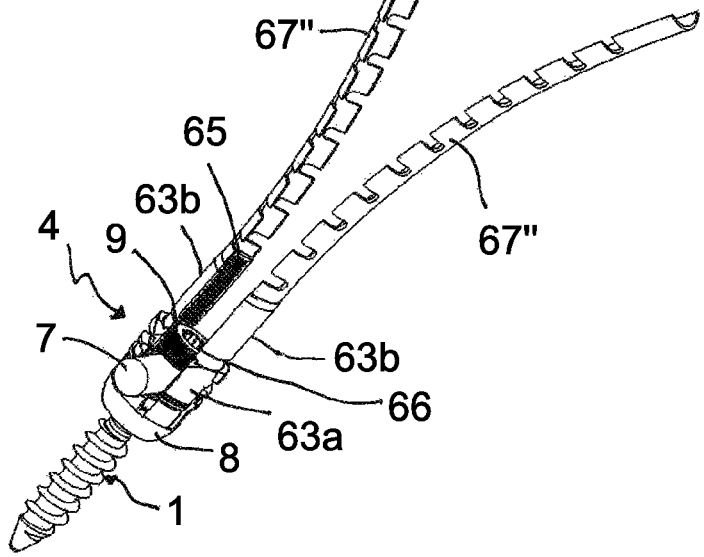
FIG. 7 shows a perspective view of the bone anchor of FIG. 6 with the extension members spread apart.

Referring to FIGS. 6 and 7, a third embodiment of the bone anchor will be described. This embodiment is similar to the first embodiment according to FIGS. 1 to 3, with the difference that the flexibility of the extended tabs 67" is achieved by providing recesses 71. The recesses 71 in this embodiment extend from a free lateral edge of the extended tabs 67" in a circumferential direction, preferably on both lateral sides of the flexible extended tabs 67", to a distance from the edge. The recesses 71 are preferably arranged in an axial direction at substantially regular distances, so that the edges have a substantially serrated shape. This results in a reduction of the stiffness of the extended tabs 67". By adapting the width and depth of the recesses 71, a desired degree of flexibility can be achieved. FIG. 7 shows the extended tabs 67" in a spread-apart condition.

Any other type of recesses or openings, for example, recesses extending fully through the wall of the extended tabs 67" or forming only partial reductions of the wall thickness may be contemplated.

Features of one of the described embodiments can be combined with features of the other embodiments to produce a variety of further embodiments. For example, the extended tabs 67" of the third embodiment according to FIGS. 6 and 7 may also be releasably mounted to the second portion 63b of the legs 63.

While the bone anchor is shown as a polyaxial bone anchor, more specifically as a bottom loader polyaxial bone anchor, the type of bone anchor can be any type, such as a top loader polyaxial bone anchor wherein the anchoring element 1 is inserted from the side of the extended tabs, or the bone anchor can be a monoaxial bone anchor where the receiving part is fixedly connected to the shank or formed monolithically with a shank to be anchored in a bone.

The bone anchor including the extension tabs may be made from bio-compatible materials, for example, of titanium or stainless steel, of a bio-compatible alloy, such as NiTi-alloys, for example Nitinol, magnesium or magnesium alloys, or from a bio-compatible plastic material, such as, for example, polyether ether ketone (PEEK) or poly-l-lactide acid (PLLA). The parts can be made of the same or of different materials. In particular, the extension tabs 67, 67',67" may be made of a material having a lower modulus of elasticity than the legs of the receiving part. The extension tabs may also be made from a superelastic NiTi alloy.

In use, usually at least two bone anchors are prepared with the extended tabs 67, 67',67" fixedly or releasably connected to an upper end of the second portion 63b of the legs 63 and implanted into a bone or a vertebra. The extended tabs 67, 67',67" project above the patient's skin and permit to guide and insert implant components, such as a spinal rod or a fixation screw or other items, in order to connect them with the bone anchor. During the surgical steps, the extended tabs 67, 67',67" can be spread apart, either manually or by the aid of an instrument. Thereby, visibility onto the implantation site is improved while a guiding function of the extended tabs is still maintained. This facilitates improved handling of surgical components. Due to the lower stiffness of the extended tabs, accidental break-off between the first and the second portions of the legs can be reduced or eliminated, and also the soft tissue is less affected.

After the spinal rod 7 has been inserted, the fixation screw 9 is guided through the extended tabs 67, 67',67" and the second portions 63b, and is screwed down until it contacts and locks the rod 7. After locking the bone anchor, the extended tabs 67, 67',67", together with the second portions 63b of the legs 63, may be broken away from the first portions 63a of the legs 63 at the break-away portion 66.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchor comprising:
   a shank for anchoring to a bone or a vertebra; and
   a receiving part for receiving a rod for coupling the rod to the shank, the receiving part having a central axis and comprising a base and two free legs extending upwardly from the base to define a recess for inserting the rod;
   wherein each of the legs comprises a first portion extending away from the base, and a second portion connected to an end of the first portion opposite the base and extending from the first portion farther away from the base, wherein a first downwardly facing engagement surface is provided on at least part of the first portion and a second downwardly facing engagement surface is provided on at least part of the second portion, wherein the first and second downwardly facing engagement surfaces are positioned at a same radial distance away from the central axis such that both are configured to engage and restrict movement of a fixation device away from the base of the receiving part to secure the rod in the recess, wherein a breakaway portion having a reduced wall thickness or width is provided between the first portion and the second portion to facilitate breaking away of the second portion from the first portion; and
   wherein each of the legs further comprises an elongate extension member connected to an end of the second portion opposite the first portion and extending from the second portion farther away from the base, wherein the extension members are at least as long axially as the second portions, and wherein when the extension members are unflexed, a greatest width between outer surfaces of the extension members is smaller than a greatest width between outer surfaces of the second portions of the legs while a distance from the central axis to an inner surface of the extension members is greater than a distance from the central axis to an inner surface of the second portions of the legs excluding the second downwardly facing engagement surface, such that a wall thickness of each of the second portions of the legs is greater than a wall thickness of each of the extension members to make the second portions of the legs stiffer than the extension members.

2. The bone anchor of claim 1, wherein the first and second downwardly facing engagement surfaces each comprises a thread.

3. The bone anchor of claim 2, wherein the inner surface of each of the extension members is threadless.

4. The bone anchor of claim 1, wherein the extension members are less stiff than the first portions of the legs.

5. The bone anchor of claim 1, wherein the extension members are radially flexible, such that the extension members are configured to be spread apart from each other.

6. The bone anchor of claim 1, wherein the extension members are torsionally flexible.

7. The bone anchor of claim 1, wherein the extension members are curved in a circumferential direction in a shape of a segment of a tube.

8. The bone anchor of claim 1, wherein for each of the legs, a wall thickness of the first portion adjacent the breakaway portion is thicker than the wall thickness of the second portion adjacent the breakaway portion.

9. The bone anchor of claim 1, wherein a wall of each of the extension members defines at least one recess configured to increase flexibility of the extension members.

10. The bone anchor of claim 1, wherein the extension members are fixedly connected to the second portions of the legs.

11. The bone anchor of claim 10, wherein the extension members are bonded or fused to the second portions of the legs.

12. The bone anchor of claim 1, wherein the extension members are configured to be removably connected to the second portions of the legs.

13. The bone anchor of claim 1, wherein for each of the legs, the extension member is configured to be connected to the second portion via a form fit connection.

14. The bone anchor of claim 1, wherein each of the extension members is configured to engage a groove provided at a free end of the second portion of each leg.

15. The bone anchor of claim 14, wherein for each of the legs, a projection or recess provided in the groove is configured to engage a corresponding recess or projection on the extension member to facilitate a form fit connection in the groove.

16. The bone anchor of claim 1, wherein the extension members are elastically flexible.

17. The bone anchor of claim 1, wherein the receiving part and the shank are fixedly connected to each other, forming a monoaxial bone anchor.

18. The bone anchor of claim 1, wherein the receiving part and the shank are configured to be pivotably connected to each other, forming a polyaxial bone anchor.

19. The bone anchor of claim 1, wherein the greatest width between outer surfaces of the second portions of the legs is smaller than a greatest width between outer surfaces of the first portions of the legs.

20. The bone anchor of claim 1, wherein the second portion of each of the legs is a solid part that extends circumferentially from one side of the receiving part to an opposite side of the receiving part and is devoid of any radially extending through holes.

21. The bone anchor of claim 1, wherein for each of the legs, a wall thickness of the first portion is the same as a wall thickness of the second portion.

22. The bone anchor of claim 1, wherein a head is formed at an end of the shank, and wherein the head is insertable into the receiving part through an opening defined at an end of the receiving part opposite the two free legs.

23. The bone anchor of claim 1, wherein a greatest outer width of the receiving part in a region that extends from the breakaway portion to a free end of the base is greater than a greatest outer width of the receiving part in a region that extends from the breakaway portion to a free end of the extension members.

24. A method of connecting a rod to a bone or a vertebra via a bone anchor comprising a shank, a receiving part, and a fixation device, the receiving part having a central axis and comprising a base and two free legs extending from the base to define a recess for inserting the rod, wherein each of the legs comprises a first portion extending upwardly away from the base, and a second portion connected to an end of the first portion opposite the base and extending from the first portion farther away from the base, wherein a first downwardly facing engagement surface is provided on at least part of the first portion and a second downwardly facing engagement surface is provided on at least part of the second portion, wherein the first and second downwardly facing engagement surfaces are positioned at a same radial distance away from the central axis such that both are configured to engage and restrict movement of the fixation device away from the base of the receiving part to secure the rod in the recess, wherein a breakaway portion having a reduced wall thickness or width is provided between the first portion and the second portion to facilitate breaking away of the second portion from the first portion, wherein each of the legs further comprises an elongate extension member connected to an end of the second portion opposite the first portion and extending from the second portion farther away from the base, wherein the extension members are at least as long axially as the second portions, and wherein when the extension members are unflexed, a greatest width between outer surfaces of the extension members is smaller than a greatest width between outer surfaces of the second portions of the legs while a distance from the central axis to an inner surface of the extension members is greater than a distance from the central axis to an inner surface of the second portions of the legs excluding the second downwardly facing engagement surface, such that a wall thickness of each of the second portions of the legs is greater than a wall thickness of each of the extension members to make the second portions of the legs stiffer than the extension members, the method comprising:

anchoring the shank to the bone or the vertebra;
inserting the rod into the recess;
engaging the fixation device with the first downwardly facing engagement surface on the legs to secure the rod in the recess; and
breaking the breakaway portions to separate the second portions of the legs and the extension members from the first portions of the legs.

* * * * *